US006255533B1

(12) United States Patent
McNabb et al.

(10) Patent No.: US 6,255,533 B1
(45) Date of Patent: Jul. 3, 2001

(54) PROCESS FOR THE RECOVERY OF CYCLOHEXANONE AND CYCLOHEXANOL FROM CYCLOHEXANONE PRODUCTION DISTILLATION BOTTOMS

(75) Inventors: Andrew J. McNabb; Deirdre R. Williams, both of Lake Jackson, TX (US)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 09/436,351

(22) Filed: Nov. 9, 1999

(51) Int. Cl.[7] ..................................................... C07C 45/29
(52) U.S. Cl. ............................ 568/366; 568/835; 568/836
(58) Field of Search .................................... 568/366, 376, 568/338, 822, 835, 836, 856, 830

(56) References Cited

U.S. PATENT DOCUMENTS

| 3,726,888 | 4/1973 | Hatten et al. ..................... 260/485.5 |
| 3,946,076 | 3/1976 | Paasen et al. ..................... 260/586 P |
| 3,974,221 | * 8/1976 | Duggan ............................ 260/586 P |
| 4,082,788 | 4/1978 | Mims ................................ 260/465.4 |
| 4,173,586 | 11/1979 | Payne et al. ..................... 260/586 R |
| 4,271,315 | 6/1981 | Cywinski ............................. 560/204 |
| 4,272,326 | 6/1981 | Hertzog et al. ......................... 203/62 |
| 4,306,944 | 12/1981 | Murthy et al. ......................... 203/77 |
| 4,316,775 | 2/1982 | Nash ....................................... 203/43 |
| 4,994,152 | 2/1991 | Kaibel et al. .......................... 203/75 |
| 5,015,787 | 5/1991 | Van Peppen ......................... 568/835 |
| 5,168,983 | 12/1992 | Tan et al. ............................... 203/29 |
| 5,874,651 | 2/1999 | McNabb et al. ..................... 568/856 |

* cited by examiner

Primary Examiner—Sreeni Padmanabhan
(74) Attorney, Agent, or Firm—Nixon & Vanderhye P.C.

(57) ABSTRACT

Organic by-products having higher boiling points than cyclohexanone (usually obtained from the bottoms of a distillation operation to separate cyclohexanone from other reaction products during cyclohexanone production) can be converted to recoverable cyclohexanone and cyclohexanol using a catalyst having high aluminum oxide concentrations. The preferred catalyst is one which has an aluminum oxide ($Al_2O_3$) content of at least about 95 wt. %, and more preferably greater than about 99 wt. %.

10 Claims, No Drawings

PROCESS FOR THE RECOVERY OF CYCLOHEXANONE AND CYCLOHEXANOL FROM CYCLOHEXANONE PRODUCTION DISTILLATION BOTTOMS

FIELD OF THE INVENTION

The present invention relates generally to the production of cyclohexanone. More specifically, the present invention relates to the recovery of cyclohexanone and cyclohexanol from distillation bottoms containing unknown by-products of cyclohexanone production.

BACKGROUND AND SUMMARY OF THE INVENTION

Cyclohexanone is a commercially important starting compound for the production of caprolactam. The production of cyclohexanone typically involves the oxidation of cyclohexane which yields cyclohexanol and cyclohexanone as the principal oxidation products. (See, U.S. Pat. No. 3,946,076, the entire content of which is expressly incorporated hereinto by reference). The production process also generates substantial quantities of by-products which have higher boiling points than cyclohexanone.

It has been proposed in the past that some of these by-products of cyclohexanone production, especially multi-cyclic ketones, can be thermally cracked into cyclohexanone and cyclohexanol. (See, U.S. Pat. No. 4,173,586, the entire content of which is incorporated hereinto expressly by reference.) It is also known that cyclohexanediols can be catalytically cracked at elevated temperatures and pressures to produce cyclohexanone and cyclohexanol. (See, U.S. Pat. No. 5,874,651, the entire content of which is incorporated hereinto expressly by reference.)

It has now been discovered that organic by-products having higher boiling points than cyclohexanone (usually obtained from the bottoms of a distillation operation to separate cyclohexanone from other reaction products during cyclohexanone production) can be converted to recoverable cyclohexanone and cyclohexanol using a catalyst having high aluminum oxide concentrations.

These, and other, aspects and advantages will become more clear after careful consideration is given to the following detailed description of the preferred exemplary embodiments thereof.

DETAILED DESCRIPTION OF THE INVENTION

The feed stream employed in the practice of the present invention includes organic by-products having higher boiling points than cyclohexanone. The preferred by-products are typically obtained from the bottoms of a distillation operation to separate cyclohexanone from other reaction products in the production of cyclohexanone by the oxidation of cyclohexane. One preferred feed stream is EP-310 ANON HEAVIES commercially available from BASF Corporation, Freeport, Tex., having the following distillation range:

| | |
|---|---|
| Initial (@ 13.5 kPa) | 110° C. |
| 10 vol. % (@ 13.5 kPa) | 135° C. |
| 20 vol. % (@ 10 kPa) | 142° C. |
| 50 vol. % (@ 4.7 kPa) | 147° C. |
| Final (75 vol. %) (@ 3.3 kPa) | 183° C. |

The preferred feed stream may includes at least about 40 wt. %, and typically between about 41.2 to about 51.0 wt. %, of higher oxidation products (i.e., organic products having a higher boiling point than cyclohexanone). Usually, the feed stream will contain between about 8.3 to about 11.8 wt. % of unknown organic constituents. In addition, the preferred feed stream may have the following components: dicyclohexylether (between about 7.8 to about 17.4 wt. %); pentyl cyclohexyl ether (between about 1.4 to about 4.4 wt. %); 1.1-bicyclohexylether (between about 0.9 to about 2.3 wt. %); 2-cyclohexylidene cyclohexanone (between about 10.0 to about 16.9 wt. %); other ketones (between about 1.2 to about 1.7 wt. %); cyclohexanol (between about 1.2 to about 7.7 wt. %); diols (between about 3.8 to about 5.6 wt. %); higher oxidation products (between about 8.0 to about 13.0 wt. %); cyclohexanone dimer (between about 1.6 to about 2.7 wt. %); and dicyclohexyloxy methane (between about 0.4 to about 0.6 wt. %).

The feed stream is brought into contact with an amount of a catalyst with a high aluminum oxide concentration suffice to convert a substantial proportion of unknown organic components in the feed stream into cyclohexanone and/or cyclohexanol. In this regard, the preferred catalyst is one which has an aluminum oxide ($Al_2O_3$) content of at least about 95 wt. %, and more preferably greater than about 99 wt. %. One particularly preferred catalyst is BASF Catalyst D 10—10 commercially available from BASF Corporation, Geismar, Louisiana, which is substantially entirely aluminum oxide with minor (i.e., less than 0.1 wt. %) of each of Na, K and Fe impurities.

According to the present invention, only relatively small, but effective amounts of the aluminum oxide-rich catalyst need to be brought into contact with the feed stream. In this regard, it is preferred that the catalyst be employed in a maximum of amount of about 10 wt. %, or more preferably about to about 2 wt. %, based on the total weight of the feed stream, and a minimum amount of about of about 0.1 wt. %, and preferably about 0.5 wt. %, based on the total weight of the feed stream.

The cyclohexanone and cyclohexanol that are obtained by the process of the present invention can be recovered conveniently by conventional distillation techniques, crystallization, or other separation processes well known to those in this art.

It is hypothesized that the increased yield is due to the increased conversion of enyl anone and other compounds to cyclohexanone and cyclohexanol. A comparison of the analysis of the feed and products from the reaction is shown below:

| Compound | EP-310 (Feed) | No catalyst Product | Invention Product (D 10-10 Catalyst) |
|---|---|---|---|
| Enyl Anone | 12.97 wt % | 1.81 wt % | 1.17 wt % |
| trans 1,2-cyclohexanediol | 1.49 wt % | 1.55 wt % | 1.17 wt % |
| RT 21.40 min | 9,105 | 7,491 | 6,250 |
| RT 25.17 min | 1,314 | 1,258 | 705 |
| RT 25.31 min | 1,439 | 382 | nd |
| RT 25.99 min | 1,605 | 279 | nd |

-continued

| Compound | EP-310 (Feed) | No catalyst Product | Invention Product (D 10-10 Catalyst) |
|---|---|---|---|
| RT 29.27 min | 1,211 | 573 | nd |
| RT 29.50 min | 1,183 | 304 | nd |

The units of measure for the compounds noted above identified by their gas chromatograph retention times (RT) are in area counts. The decrease in area counts of the RT compounds above indicates that the addition of the aluminum oxide-rich (D10—10) catalyst promotes a reaction which consumes some or all of the RT compound.

The present invention will be further understood from the following non-limiting Examples.

EXAMPLES

Laboratory cracking tests were conducted using a Parr Bomb. Specifically, the materials recovered after each Parr Bomb were separated and the organics analyzed using a Hewlett-Packard 5890 Series II gas chromatograph (GC) with a CP Sil 8 CB column, 25 M×0.15 mm6x 1.2 pm thickness. Helium was the carrier gas. The temperature program began at 90° C. and held for 0.00 min. The first ramp was at 5° C./min up to 190° C. and held for 0.00 min. The last ramp was at 10.0° C./min up to 275° C. and held for 11.50 mins. All samples were diluted in acetone prior to injection.

Example 1

A mixture of 297.28 g of EP-310 and 29.98 g of water was reacted in a Parr Bomb. The reaction temperature was 300° C., the pressure was 1,525 psig, and the residence time was 60 minutes. The final product contained 3.07 wt % cyclohexanol and 10.60 wt % cyclohexanone for a total anolon concentration of 13.67 wt %.

Example 2

Using material from the same batch as the material used in Example 1, a mixture of 328.02 g of EP-310 and 37.90 g of water was reacted in a Parr Bomb. The reaction temperature was 300° C., the pressure was 1,600 psig, and the residence time was 60 minutes. The final product contained 3.49 wt % cyclohexanol and 13.14 wt % cyclohexanone for a total anolon concentration of 16.63 wt %.

Example 3

Using material from the same batch as the material used in Example 1, a mixture of 310.98 g of EP-310, 44.23 g of water, and 1.7 g of KOH was reacted in a Parr Bomb. The reaction temperature was 300° C., the pressure was 1650 psig, and the residence time was 60 minutes. The final product contained 3.40 wt % cyclohexanol and 13.30 wt % cyclohexanone for a total anolon concentration of 16.70 wt %.

Example 4

Using material from the same batch as the material used in Example 1, a mixture of 284.46 g of EP-310, 27.18 g of water, 1.88 g of KOH, and 2.84 g of D10—10 catalyst was reacted in a Parr Bomb. The reaction temperature was 300° C., the pressure was 1,400 psig, and the residence time was 60 minutes. The final product contained 4.11 wt % cyclohexanol and 14.89 wt % cyclohexanone for a total anolon concentration of 19.0 wt %.

Example 5

A compound with a gas chromatograph retention time of 21.40 minutes was reacted in a Parr Bomb which contains D10—10 catalyst. The reaction temperature was 300° C., the pressure was 1,400 psig, and the residence time was 60 minutes. Gas chromatograph analysis showed the starting material had 9,105 area counts and the product had 6,250 area counts.

Example 6

A compound with a gas chromatograph retention time of 25.17 minutes was reacted in a Parr Bomb which contains D10—10 catalyst. The reaction temperature was 300° C., the pressure was 1,400 psig, and the residence time was 60 minutes. Gas chromatograph analysis showed the starting material had 1,314 area counts and the product had 705 area counts.

Example 7

A compound with a gas chromatograph retention time of 25.31 minutes was reacted in a Parr Bomb which contains D10—10 catalyst. The reaction temperature was 300° C., the pressure was 1,400 psig, and the residence time was 60 minutes. Gas chromatograph analysis showed the starting material had 1,440 area counts and the product had no detectable area counts.

Example 8

A compound with a gas chromatograph retention time of 25.99 minutes was reacted in a Parr Bomb which contains D10—10 catalyst. The reaction temperature was 300° C., the pressure was 1,400 psig, and the residence time was 60 minutes. Gas chromatograph analysis showed the starting material had 1,605 area counts and the product had no detectable area counts.

Example 9

A compound with a gas chromatograph retention time of 29.27 minutes was reacted in a Parr Bomb which contains D10—10 catalyst. The reaction temperature was 300° C., the pressure was 1,400 psig, and the residence time was 60 minutes. Gas chromatograph analysis showed the starting material had 1,211 area counts and the product had no detectable area counts.

Example 10

A compound with a gas chromatograph retention time of 29.50 minutes was reacted in a Parr Bomb which contains D10—10 catalyst. The reaction temperature was 300° C., the pressure was 1,400 psig, and the residence time was 60 minutes. Gas chromatograph analysis showed the starting material had 1,184 area counts and the product had no detectable area counts.

The Examples above clearly indicate how the addition of a small amount of an aluminum oxide-rich catalyst results in improved process yields.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for the recovery of cyclohexanone and cyclohexanol from a by-product stream of cyclohexanone production containing organic constituents with a higher boiling point as compared to cyclohexanone, the process comprising subjecting the by-product stream to catalytic cracking conditions in the presence of a high aluminum oxide-containing catalyst.

2. The process of claim 1, wherein the catalysts has an aluminum oxide ($Al_2O_2$) content of at least about 95 wt. %.

3. The process of claim 1, wherein the catalysts has an aluminum oxide ($Al_2O_2$) content of at least about 99 wt. %.

4. The process of claim 1, wherein the catalyst contains substantially entirely aluminum oxide, with a minor amount of impurities.

5. The process of claim 4, wherein each of the impurities is present in an amount less than about 0.1 wt. %.

6. The process of claim 3, 4 or 5, wherein the impurities include at least one selected from the group consisting of Na, K and Fe.

7. The process of claim 1, wherein the by-product stream contains at least about 40 wt. % of said organic constituents with a higher boiling point as compared to cyclohexanone.

8. The process of claim 1 or 7, wherein the process stream contains at least one constituent selected from the group consisting of dicyclohexylether; pentyl cyclohexyl ether; 1,1-bicyclohexylether; 2-cyclohexylidene cyclohexanone; cyclohexanol; cyclohexanone dimer; and dicyclohexyloxy methane.

9. The process of claim 1, wherein the catalyst is present in an amount between about 0.1 wt. % to about 10 wt. %, based on total weight of the by-product stream.

10. The process of claim 1, wherein the catalyst is present in an amount between about 0.5 wt. % to about 2 wt. %, based on total weight of the by-product stream.

* * * * *